(12) United States Patent
Mourier et al.

(10) Patent No.: US 8,546,354 B2
(45) Date of Patent: Oct. 1, 2013

(54) ACYLATED DECASACCHARIDES AND THEIR USE AS ANTITHROMBOTIC AGENTS

(75) Inventors: Pierre Mourier, Paris (FR); Christian Viskov, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/288,585

(22) Filed: Nov. 3, 2011

(65) Prior Publication Data

US 2012/0108544 A1    May 3, 2012

Related U.S. Application Data

(63) Continuation of application No. PCT/IB2010/051935, filed on May 4, 2010.

(30) Foreign Application Priority Data

May 5, 2009    (EP) .................................... 09290319

(51) Int. Cl.
*A61K 31/727*    (2006.01)
*A61P 7/02*    (2006.01)
*C08B 37/10*    (2006.01)

(52) U.S. Cl.
USPC .............................................. 514/56; 536/21

(58) Field of Classification Search
USPC .............................................. 514/56; 536/21
See application file for complete search history.

(56) References Cited

U.S. PATENT DOCUMENTS

| | | | | |
|---|---|---|---|---|
| 4,401,662 A | * | 8/1983 | Lormeau et al. | 514/56 |
| 4,801,583 A | | 1/1989 | Petitou et al. | |
| 4,826,827 A | * | 5/1989 | Lormeau et al. | 514/56 |
| 6,617,316 B1 | * | 9/2003 | Mourier et al. | 514/56 |

FOREIGN PATENT DOCUMENTS

WO    WO2010/128450 A1    11/2010

OTHER PUBLICATIONS

Guerrini et al, Journal of Biol. Chem. 2008, 283(39), 26662-75.*
Petitou, et al., 1976-1983, a Critical Period in the History of Heparin: The Discovery of the Antithrombin Binding Site, Biochimie, vol. 85, (2003), pp. 83-89.
Guerrini, et al., Antithrombin-Binding Octasaccharides and Role of Extensions of the Active Pentasaccharide Sequence in the Specificity and Strength of Interaction Evidence for Very High Affinity Induced by an Unusual Glucuonic Acid Residue. The Journal of Biological Chemistry, vol. 283, No. 39, pp. 26662-26675, (2008).
Hook, et al., Anticoagulant activity of heparin: Separation of high-activity and low-activity heparin species by affinity chromatography on immobilized antithrombin, FEBS Letters, vol. 66, Issue 1, Jul. 1, 1976, pp. 90-93.
Linhardt, 2003 Claude S. Hudson Award Address in Carbohydrate Chemistry. Heparin: Structure and Activity, Journal of Medicinal Chemistry, vol. 46, No. 13, (2003), pp. 2551-2564.
Mourier, et al., Chromatographic Analysis and Sequencing Approach of Heparin Oligosaccharides Using Cetyltrimethylammonium Dynamically Coated Stationary Phases, Analytical Biochemistry, vol. 332, (2004), pp. 299-313.

* cited by examiner

*Primary Examiner* — Shaojia Anna Jiang
*Assistant Examiner* — Ganapathy Krishnan
(74) *Attorney, Agent, or Firm* — Scully, Scott, Murphy & Presser, P.C.

(57) ABSTRACT

The instant invention relates to decasaccharides of formula (I):

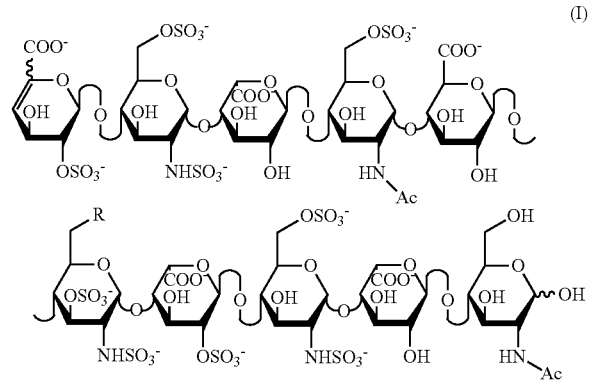

wherein Ac represents an acetyl group and R represents a group of formula —OH or —$OSO_3^-$, in their acid form or in the form of any one of their pharmaceutically acceptable salts, and to their process of preparation. The oligosaccharides of formula (I) are useful as antithrombotic agents.

12 Claims, No Drawings

ACYLATED DECASACCHARIDES AND THEIR USE AS ANTITHROMBOTIC AGENTS

The instant invention relates to novel oligosaccharides, more specifically acylated decasaccharides, and to their use as antithrombotic agents.

Clotting is a defense mechanism preventing excessive loss of blood and ingestion of microbes. Yet, inadvertent formation and dislocation of clots may be harmful; antithrombotic drugs prevent the formation and growth of clots.

Heparin and Low Molecular Weight Heparins (LMWHs) are the current standard therapy in the management of thromboembolic diseases. Their anticoagulant activity is exerted through inhibition of coagulation factors, mainly activated factor X (FXa) and thrombin (factor IIa). This inhibitory action is mediated by the specific interaction of heparin species with antithrombin (AT), a serine protease inhibitor of the serpin family.

These drugs derive from animal sources: unfractionated heparin (UFH) is isolated from tissues such as lungs or intestinal mucosa, from porcine or bovine origins. LMWHs, such as tinzaparin, ardeparin, dalteparin, enoxaparin, nadroparin or reviparin, are obtained by enzymatic or chemical depolymerization of heparin.

Heparin and LMWHs are complex mixtures of molecules: they contain numerous sulfated polysaccharides, each of them being a polymer composed of a linear chain of monosaccharide residues. Therefore, the different polysaccharides present in heparin and in LMWHs vary in their lengths as well as in their chemical structures. The varying degree of sulfation and the presence of different 1→4 linked uronic acid and glucosamine disaccharide units give rise to a complex overall structure (J. Med. Chem., 2003, 46, 2551-2554).

Another class of antithrombotic drugs consists in synthetic oligosaccharides. Indeed, in the early 1980s it was determined that a unique pentasaccharide domain in some heparin chains is the minimal sequence required for binding and activating antithrombin III (Biochimie, 2003, 85, 83-89). Fondaparinux sodium is a synthetic analogue of this pentasaccharide, obtained through more than 60 steps of chemical synthesis. It is a selective inhibitor of factor Xa, commercialized for the prevention of thrombosis after orthopedic and abdominal surgery, for the prevention and treatment of deep vein thrombosis and pulmonary embolism, as well as for the treatment of coronary diseases.

Structure-based design has subsequently led to analogues with longer duration of action, such as idraparinux, displaying either selective factor Xa or dual Xa and IIa inhibition properties. The search for improved pharmacodynamic profiles lead to the synthesis of longer oligosaccharides, such as the clinical candidate SR123781 (hexadecasaccharidic compound), aiming at providing heparin mimetics that are more potent than heparin as regards antithrombin activity, but devoid of its side effects.

The Applicant has devised a novel approach for the identification of new antithrombotic compounds. Starting from oligosaccharides mixtures of LMWHs, specific analytical and separation methods have permitted to isolate oligosaccharides endowed with advantageous antithrombotic properties, useful in anticoagulant therapy.

The oligosaccharides according to the instant invention respond to the formula (I):

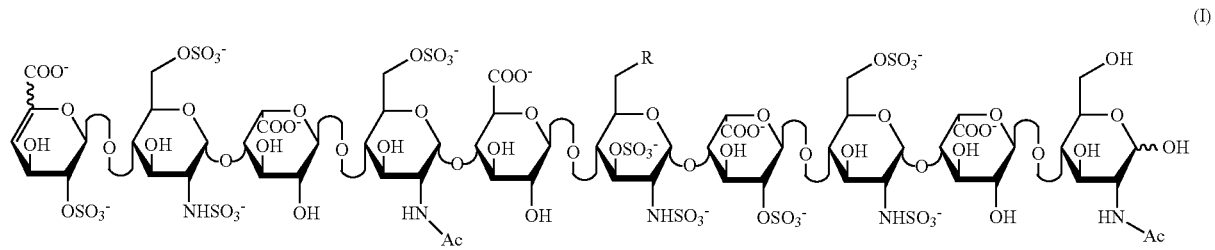

(I)

wherein Ac represents an acetyl group (i.e. a group of formula —$COCH_3$), R represents a group of formula —OH or —$OSO_3^-$, and wherein the wavy lines denote bonds situated either below or above the plane of the pyranose rings.

The oligosaccharides of formula (I) are decasaccharides. The invention encompasses the decasaccharides of formula (I) in their acid form or in the form of any one of their pharmaceutically acceptable salts. In the acid form, the carboxylate (—$COO^-$) and sulphate (—$SO_3^-$) functional groups are respectively in the —COOH and —$SO_3H$ forms.

The term "pharmaceutically acceptable salt" of the oligosaccharides of formula (I) is understood to mean an oligosaccharide in which one or more of the —$COO^-$ and/or —$SO_3^-$ functional groups are bonded ionically to a pharmaceutically acceptable cation. The preferred salts according to the invention are those for which the cation is chosen from the cations of alkali metals and more preferably still those for which the cation is sodium ($Na^+$).

The invention more specifically relates to the oligosaccharides of formula (Ia) and (Ib) below:

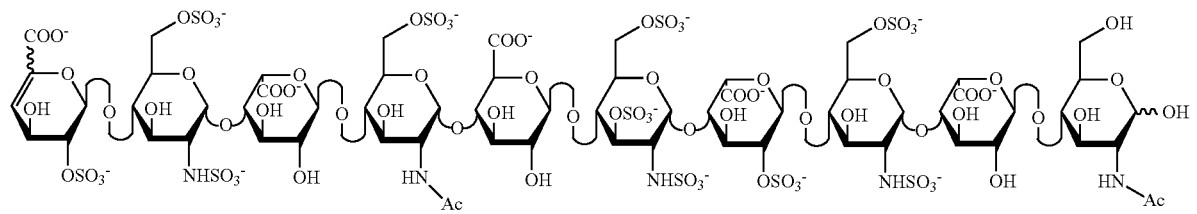

(Ia)

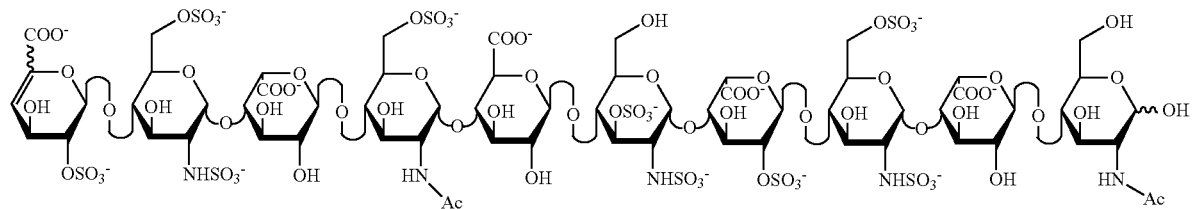

(Ib)

The oligosaccharide of formula (Ia) corresponds to the decasaccharide of formula (I) wherein R represents a group of formula —$OSO_3^-$, whereas the oligosaccharide of formula (Ib) corresponds to the decasaccharide of formula (I) wherein R represents a group of formula —OH.

In accordance with the present invention, the compounds of formula (I) can be obtained from a LMWH product by using orthogonal (combined) separation methods selected from Gel Permeation Chromatography (GPC), AT affinity chromatography and High Performance Liquid Chromatography (HPLC), including dynamically coated anion exchange chromatography and covalent anion exchange chromatography. According to the invention, these separation methods may be used in any possible combination thereof.

Gel Permeation Chromatography can be performed on columns filled with Bio Gel P30 (Bio-Rad) circulated with $NaClO_4$. Selected fractions are desalted, using techniques known in the Art.

AT affinity chromatography can be performed on columns filled with AT-Sepharose. The stationary phase is prepared by coupling human AT (1 g; Biomed) to CNBr-activated Sepharose 4B (Sigma). The methodology of Höök et al. (FEBS Letters, 1976, 66(1), 90-3) is used to prepare the AT column, which is eluted using a NaCl gradient.

Dynamically coated anion exchange chromatography HPLC is achieved using CTA-SAX chromatography (dynamic anion exchange chromatography with cetyltrimethylammonium). CTA-SAX semi-preparative columns were coated as described by Mourier, P. A. J. and Viskov, C. (Analytical Biochem., 2004, 332, 299-313) on columns filled with Hypersil BDS C18 (5 μm). Column coating is performed as for the analytical columns, by percolating cetyltrimethylammonium hydrogen sulfate solutions in water/methanol. Mobile phases are aqueous sodium methanesulfonate at concentrations varying between 0 and 2.5 M. The pH is adjusted to 2.5 by addition of diluted methanesulfonic acid. Collected fractions are neutralized and desalted on Sephadex G-10 after a preliminary treatment on Mega Bondelut C18 cartridges (Varian).

Covalent anion exchange chromatography can be achieved using anions exchange on AS11 (Dionex) semi-preparative HPLC columns. Any other anion exchange method may be performed, using other columns than Dionex AS11.

A final step for desalting the oligosaccharide thus obtained is performed, after neutralization of the collected fractions, in order to recover the oligosaccharide of the invention with the desired salt form. Methods for desalting oligosaccharides are well known to one of skill in the Art; mention may be made for example of desalting on a Sephadex G-10 column.

The following protocols describe in detail an example for the preparation of the compounds (Ia) and (Ib) according to the invention, in the form of sodium salts. They are included herewith for purposes of illustration only and are not intended to be limiting of the invention.

In this example, the compounds (Ia) and (Ib) are prepared from a starting LMWH product by performing the following steps: Gel Permeation Chromatography (GPC), then ATIII affinity chromatography, then CTA-SAX chromatography (dynamically coated anion exchange chromatography), and then covalent anion exchange chromatography.

About 140 g of enoxaparin (commercially available from sanofi-aventis) are injected in about 60 runs in gel permeation, on columns (200 cm×5 cm) filled with Bio Gel P30 and circulated with $NaClO_4$ 0.2 M at 100 ml/h. Each run lasts about 24 hours. The decasaccharide fraction is gathered and desalted on a column filled with Sephadex G-10 (100 cm×7 cm), circulated with water, to obtain about 18 g of said fraction.

The entire decasaccharide fraction is injected in ATIII affinity chromatography in about 36 runs where about 500 mg are injected on 30 cm×5 cm columns. The low-affinity portion is eluted from the column with a 0.25 M NaCl solution buffered at pH 7.4 with 1 mM Tris at 6 ml/min. The high-affinity decasaccharide fraction is eluted with a step gradient of NaCl (0.7, 1.15, 1.6, 2.05, 2.65 and 3 M NaCl in 1 mM Tris-HCl, pH 7.4). The NaCl gradient is monitored by the conductivity and the detection is in UV at 232 nm.

Decasaccharides eluted in affine fractions with conductivities between 85 and 120 mS/cm are gathered, desalted on Sephadex G-10, and used as starting material for the next purification, achieved in CTA-SAX semi preparative chromatography (250 mm×22 mm columns). Column coating is performed by percolating 1 mM cetyltrimethylammonium hydrogen sulfate solutions in water/methanol (17:8, v/v) for 4 h with the column temperature adjusted to 45° C. Mobile phases are aqueous sodium methanesulfonate (Interchim) at concentrations varying between 0 and 2.5 M. The pH is adjusted to 2.5 by addition of diluted methanesulfonic acid. Separations are achieved at 40° C. Salt concentration in the mobile phase is increased linearly from 0 to 2.5 M over 60 min. Flow rate is 20 ml/min and UV detection at 234 nm is used.

About 250 mg are injected in 5 separate runs where 50 mg of the affine fraction are injected on the column. Fractions obtained are controlled on CTA-SAX analytical columns (150×2.1 mm Hypersil BDS C18 (3 μm)) after neutralization. Fractions are gathered, passed through Mega Bondelut C18 cartridges (Varian) and desalted on Sephadex G-10.

After that step, the decasaccharides of formula (Ia) and (Ib) are obtained in mixture, with insufficient purity. Their final separation and purification is achieved on AS11 (Dionex) HPLC semi preparative columns, circulated with a NaClO$_4$ concentration gradient. Fractions containing the decasaccharides (Ia) and (Ib) are controlled on Dionex AS11 analytical columns (250×2.1 mm) and desalted on Sephadex G-10. Their proton NMR analyses, performed on a BRUCKER apparatus (600 MHz), are as follows.

Decasaccharide (Ia):
NMR $^1$H in D$_2$O (δ in ppm): 2.05 (3H, s), 3.29 (2H, m,), 3.40 (1H, t, 6 Hz), 3.46 (1H, dd, 8 et 2 Hz), entre 3.65 et 4.55 (31H, m), 4.61 (1H, d, 6 Hz), 4.80 (3H, m), 5.06 (1H, d, 2 Hz), 5.09 (1H, d, 2 Hz), 5.17 (1H, d, 6 Hz), 5.27 (1H, d, 2 Hz), 5.36 (2H, m), 5.43 (1H, d, 2 Hz), 5.45 (1H, d, 2 Hz), 5.53 (1H, d, 2 Hz), 5.81 (1H, d, 4 Hz).

Decasaccharide (Ib):
NMR $^1$H in D$_2$O (δ in ppm): 2.04 (6H, s), 3.27 (2H, m), 3.42 (2H,m), entre 3.60 et 4.50 (40H, m), 4.55 (1H, d, 6 Hz), 4.62 (1H, s), 4.80 (3H, m), 4.97 (1H, s), 5.02 (1H, s), 5.20 (1H, d, 2 Hz), 5.35 (1H, d, 2 Hz), 5.38 (2H, m), 5.50 (2H, m), 5.53 (1 H, s), 5.98 (1 H, d, 4 Hz).

The oligosaccharides of the invention underwent pharmacological studies which demonstrated their antithrombotic properties and their value as therapeutically active substances.

Anti-FXa Activity in Plasma:

The ability of the sodium salt of the oligosaccharides (I) to accelerate AT-mediated FXa inhibition was analyzed in nearly physiological conditions. The anti-FXa activity measurement was performed using the competitive chromogenic assay STA®-Rotachrom® Heparin (Diagnostica Stago Inc.) automated on a STA®-R analyzer (Diagnostica Stago Inc.) according to the manufacturer's recommendation. Bovine FXa (Diagnostica Stago Inc.) was used. Fondaparinux was the reference material, obtained from commercial source marketed by GlaxoSmithKline. It was spiked at increasing concentrations (0.0218-0.0460-0.0872-0.1740-0.3490-0.4650 μmol/L) in normal pool human plasma (Hyphen). Dose response linearity was demonstrated. The oligosaccharides of the invention and fondaparinux were tested at 6 concentrations ranging from 0.0218 to 0.4650 μM. The concentration of AT in plasma milieu was 2.25 μM. The measured absolute anti-Xa activity of the purified oligosaccharides was expressed in IU/ml, according to European Pharmacopeia 6.0 (01/2008:0828). The relative anti-FXa activity was calculated from the ratio of the absolute activity versus that of fondaparinux.

In this test, the oligosaccharides (Ia) and (Ib) of the invention display absolute anti-FXa activities of 1.13 and 1.14 IU/ml, respectively. Their relative anti-Xa activities compared to fondaparinux are 1.40 and 1.37 fold, respectively.

The oligosaccharides of formula (I) according to the invention therefore display high antithrombotic properties. They can be useful for the preparation of drugs, specifically of antithrombotic drugs. Therefore, another object of the invention is a medicament, which comprises an oligosaccharide of formula (I) or an addition salt thereof with a pharmaceutically acceptable salt.

Such a medicament is useful in therapeutics, in particular in the treatment and prevention of thromboses, including venous thromboses (for example in the post-operative phase of surgical patients, in cancer patients or in medical patients with restricted mobility) and acute arterial thrombotic events, in particular in the case of myocardial infarction.

Another object of the invention is also a pharmaceutical composition, which comprises, as active principle, an oligosaccharide of formula (I) according to the present invention. Such a pharmaceutical composition comprises an effective dose of an oligosaccharide of formula (I) according to the invention, or an addition salt thereof with a pharmaceutically acceptable salt, and at least one pharmaceutically acceptable excipient. Said excipients are chosen according to the pharmaceutical form and the administration route desired, among usual excipients known to one of skill in the art.

The pharmaceutical compositions according to the invention may comprise, in addition to the oligosaccharide of formula (I), at least one other active principle selected from antithrombotic oligosaccharides, whether synthetic compounds (obtained by chemical, stepwise synthesis starting from appropriate mono- or oligosaccharidic building blocks) or compounds isolated from heparin or LMWHs sources.

In the pharmaceutical compositions according to the invention for the oral, sublingual, sub-cutaneous, intramuscular, intra-venous, topical, local, intratracheal, intranasal, transdermal or rectal administration, the active principle of formula (I) above, or its salt, can be administered as a unitary dosage form, in blend with usual pharmaceutical excipients, to animals and human beings for the prevention or for the treatment of the pathologies mentioned above.

The appropriate unitary dosage forms comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intramuscular or intra-venous forms, the rectal forms and the implants. For the topical application, the compound of the invention may be used as creams, gels, ointments or lotions.

The present invention, according to another of its aspects, also relates to a method for the treatment and prevention of the above pathologies, which comprises the administration to a patient of an effective dose of an oligosaccharide of formula (I) according to the invention, or a salt with a pharmaceutically acceptable salt thereof.

The invention claimed is:

1. An isolated and purified oligosaccharide of formula (I):

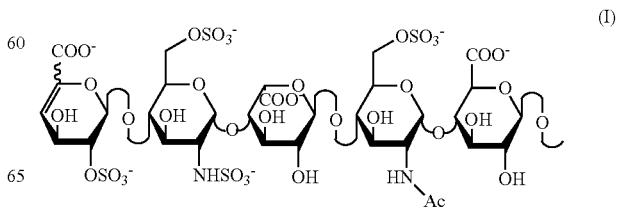

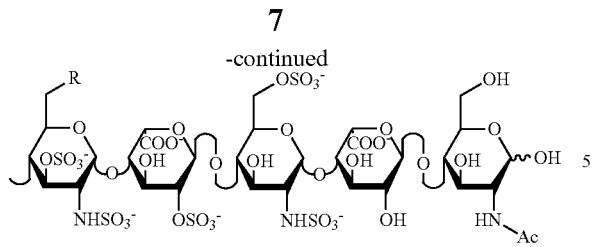

wherein Ac represents an acetyl group, R represents a group of formula —OH or —OSO$_3^-$, and wherein the wavy lines denote bonds situated either below or above the plane of the pyranose rings,
in its acid form or in the form of any one of its pharmaceutically acceptable salts.

2. An oligosaccharide according to claim 1, wherein R represents a group of formula —OSO$_3^-$.

3. An oligosaccharide according to claim 1, wherein R represents a group of formula —OH.

4. An oligosaccharide according to claim 1, in the form of its sodium salt.

5. A process for the preparation of an oligosaccharide according to claim 1, which comprises steps for separating said oligosaccharide from a starting Low Molecular Weight Heparin (LMWH) product by performing Gel Permeation Chromatography (GPC), AT affinity chromatography, dynamically coated anion exchange chromatography (CTA-SAX) and covalent anion exchange chromatography, in any possible combination of those methods.

6. The process according to claim 5, which comprises the following steps:
   a) Gel Permeation Chromatography (GPC), then
   b) AT affinity chromatography, then
   c) dynamically coated anion exchange chromatography (CTA-SAX), and then
   d) covalent anion exchange chromatography.

7. The process according to claim 5, wherein the anion exchange chromatography is performed on Dionex AS 11 HPLC columns.

8. The process according to claim 5, wherein the starting Low Molecular Weight Heparin (LMWH) product is enoxaparin.

9. A pharmaceutical composition, comprising an oligosaccharide of formula (I) according to claim 1, or a pharmaceutically acceptable addition salt thereof, and at least one pharmaceutically acceptable excipient.

10. The pharmaceutical composition according to claim 9, further comprising at least one other active principle selected from antithrombotic oligosaccharides.

11. A method for the treatment of thromboses in a patient comprising administering to the patient an oligosaccharide of formula (I) according to claim 1, or a pharmaceutically acceptable addition salt thereof.

12. The method according to claim 11, wherein the thromboses are venous thromboses or acute thrombotic events.

* * * * *